United States Patent [19]

Ellingboe et al.

[11] Patent Number: 5,256,654
[45] Date of Patent: Oct. 26, 1993

[54] SUBSTITUTED PYRROLOPYRIMIDINES, AZEPINOPYRIMIDINES AND PYRIDOPYRIMIDINES USEFUL AS ANGIOTENSIN II ANTAGONISTS

[75] Inventors: John W. Ellingboe, Princeton; Madelene Nikaido, Plainsboro; Jehan Bagli, Princeton, all of N.J.

[73] Assignee: American Home Products Corporation, New York, N.Y.

[21] Appl. No.: 901,485

[22] Filed: Jun. 25, 1992

Related U.S. Application Data

[63] Continuation-in-part of Ser. No. 782,025, Oct. 24, 1991, Pat. No. 5,149,699.

[51] Int. Cl.$^5$ .................. A61K 31/505; A61K 31/55; C07D 487/04; C07D 471/04
[52] U.S. Cl. ........................ 514/186; 514/258; 544/225; 544/280
[58] Field of Search ............. 544/280, 225; 514/186, 514/258

[56] References Cited

U.S. PATENT DOCUMENTS 4,916,129  4/1990  Carini ............................. 514/235.2
5,039,814  8/1991  Shuman ........................... 548/228

FOREIGN PATENT DOCUMENTS 0253310  1/1988  European Pat. Off. .
0323841  7/1989  European Pat. Off. .
0324377  7/1989  European Pat. Off. .
0401030  5/1990  European Pat. Off. .
0411507  2/1991  European Pat. Off. .
0412594  2/1991  European Pat. Off. .
0415886  3/1991  European Pat. Off. .
0419048  8/1991  European Pat. Off. .

OTHER PUBLICATIONS

Santilli, J. Het. Chem. 13, 135(1976).

Primary Examiner—Mark L. Berch
Attorney, Agent, or Firm—Walter Patton

[57] ABSTRACT

This invention relates to pyrrolo-, pyrido-, azepino-, and azocinopyrimidines of the general formula I

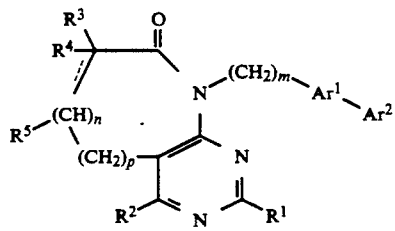

wherein $R^1$, $R^2$, $R^3$, and $R^4$ are independently H, lower alkyl containing 1 to 6 carbon atoms, or perfluoroalkyl containing 1 to 6 carbon atoms; $R^5$ is H or when n is 1 $R^5$ taken together with $R^3$ comprises a double bond; n is 0 to 1; p is 0 to 2; m is 0 to 3; $Ar^1$ is

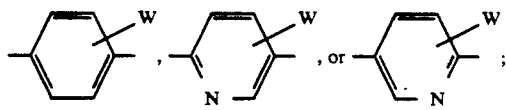

wherein W is H, lower alkyl containing 1 to 6 carbon atoms, halogen, hydroxy, or lower alkoxy containing 1 to 6 carbon atoms; $Ar^2$ is

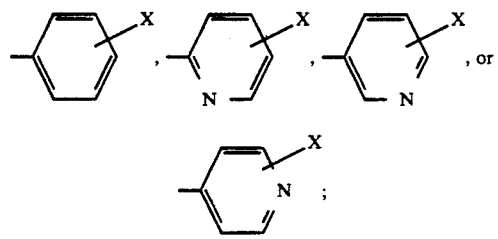

wherein X is (Abstract continued on next page.)

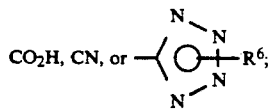

wherein $R^6$ is H, tert-butyl, tri-n-butylstannyl, or triphenylmethyl; and the pharmaceutically acceptable salts thereof which by virtue of their ability to antagonize angiotensin II are useful for the treatment of hypertension, congestive heart failure, and restenosis. The compounds are also useful for reducing lipid levels in the blood plasma and are thus useful for treating hyperlipidemia and hypercholesterolemia. Also disclosed are processes for the production of said compounds and pharmaceutical compositions containing said compounds.

8 Claims, No Drawings

SUBSTITUTED PYRROLOPYRIMIDINES, AZEPINOPYRIMIDINES AND PYRIDOPYRIMIDINES USEFUL AS ANGIOTENSIN II ANTAGONISTS

This is a continuation-in-part divisional application of copending application of U.S. Ser. No. 07/782,025, filed Oct. 24, 1991, issued as U.S. Pat. No. 5,149,699, on Sep. 22, 1992.

BACKGROUND OF THE INVENTION

This invention relates to substituted pyrimidines which are useful for the treatment of hypertension. They achieve this by antagonizing the effects of angiotensin II; the active component of the renin angiotensin system.

Angiotensinogen is converted to angiotensin I by the action of the enzyme renin. Angiotensin II (A II) is formed by angiotensin converting enzyme (ACE) acting on angiotensin I. A II is a powerful vasoconstrictor and is implicated as the cause of high blood pressure in a number of species including man. A II elicits these vasopressor responses by acting at specific receptor sites. The compounds described in this invention compete with A II for these receptor sites, thus antagonizing the vasopressor effects of A II.

PRIOR ART

E. E. Allen et al. disclose N-substituted oxopyrimidines in EP 0419048 A.

E. E. Allen et al. describe 4-oxo-quinazolines in EP 0411766 A.

D. A. Roberts et al. describe quinoline ethers in EP 0412848 A.

D. J. Carini et al. describe N-substituted benzimidazoles in U.S. Pat. No. 4,880,804. P. Chakravarty et al. disclose similar imidazole structures in EP 0401030 A where the phenyl aromatic ring is replaced by a seven membered heterocycle. Azabenzimidazoles are described by P. Herold et al. in EP 0415886 A.

D. J. Carini el al. disclose N-substituted imidazoles in EP 0253310, EP 0324377, and U.S. Pat. No. 4,916,129.

D. J. Carini et al. disclose in EP 0323841 N-substituted pyrazoles, pyrroles and triazoles. Similar pyrazole derivatives are disclosed by T. Naka et al. in EP 0411507 A and additional triazoles are described by L. L. Chang et al. in EP 0412594 A.

All of the above are claimed as A II antagonists.

The compounds of this invention differ from the above mentioned prior art in that they contain a pyrimidine ring fused to a pyrrolone, pyridinone, azepinone, or azocinone ring. Except for the first reference (E. E. Allen et al. EP 0419048 A), the non-peptidic A II antagonists disclosed in the above mentioned prior art are all nitrogenous 5-membered rings, either isolated or fused to phenyl rings, or nitrogenous 6-membered rings fused to phenyl rings. The compounds in EP 0419048 A are pyrimidin-4-ones.

R. F. Shuman et al. disclose in U.S. Pat. No. 5,039,814 a process for the synthesis of 2-substituted 1-(tetrazol-5-yl)benzenes which comprises the directed ortholithiation of 1-(tetrazol-5-yl)benzenes and subsequent reaction of the lithiated intermediate with an electrophile. The triphenylmethyl group is used as a protecting group on the tetrazole.

The process of the present invention differs in that a 2-bromo-1-(tetrazol-5-yl)aryl protected with a tert-butyl group is converted to a 2-(tetrazol-5-yl)arylboronic acid directly by the addition of Mg and a trialkylborate concurrently.

DESCRIPTION OF THE INVENTION

This invention relates to substituted pyrimidines of formula I:

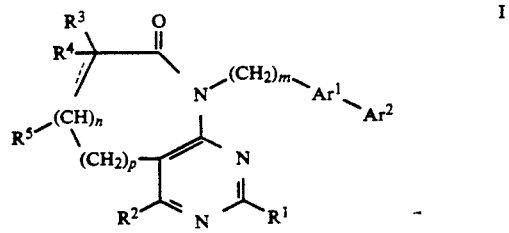

wherein $R^1$, $R^2$, $R^3$, are independently H, lower alkyl containing 1 to 6 carbon atoms, or perfluoroalkyl containing 1 to 6 carbon atoms; $R^5$ is H or when n is 1 $R^5$ taken together with $R^3$ comprises a double bond; n is 0 to 1; p is 0 to 2; m is 0 to 3; $Ar^1$ is

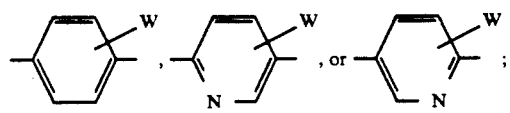

where W is H, lower alkyl containing 1 to 6 atoms, halogen, hydroxy, or lower alkoxy containing 1 to 6 carbon atoms; $Ar^2$ is

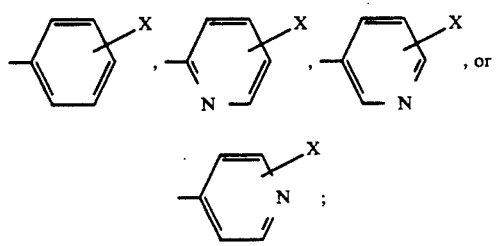

wherein X is

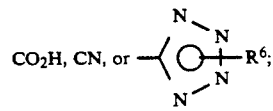

wherein $R^6$ is H, tert-butyl, tri-n-butylstannyl, or triphenylmethyl; and the pharmaceutically acceptable salts thereof.

A more preferred aspect of the present invention is represented by general formula II:

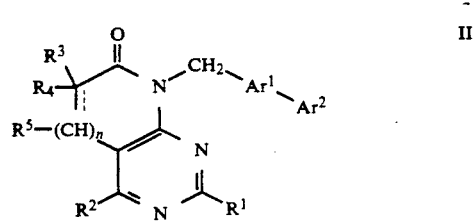

wherein $R^1$, $R^2$, $R^3$, and $R^4$ are independently H, lower alkyl containing 1 to 6 carbon atoms, or perfluoroalkyl containing 1 to 6 carbon atoms; $R^5$ is H or when n is 1 $R^5$ taken together with $R^3$ comprises a double bond; n is 0 to 1; $Ar^1$ is

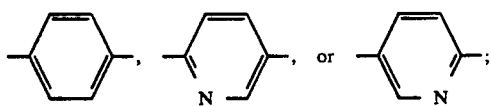

$Ar^2$ is

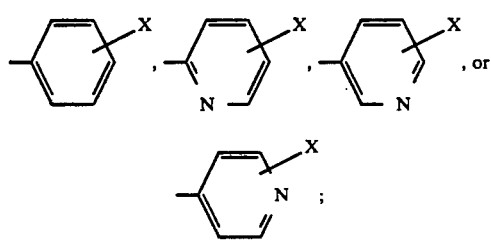

wherein X is

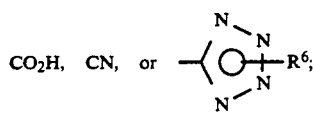

wherein $R^6$ is H, tert-butyl, tri-n-butylstannyl, or triphenylmethyl; and the pharmaceutically acceptable salts thereof.

A still more preferred aspect of the present invention is represented by the general formula III:

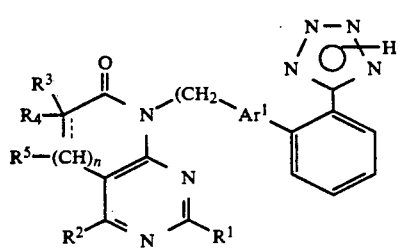

wherein $R^1$, $R^2$, $R^3$, and $R^4$ are independently H, methyl, trifluoromethyl; $R^5$ is H or when n is 1 $R^5$ taken together with $R^3$ comprises a double bond; n is 0 to 1; $Ar^1$ is

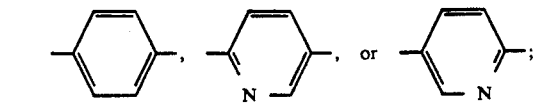

and the pharmaceutically acceptable salts thereof.

The most preferred aspects of the present invention are:

2,4-dimethyl-5,7-dihydro-7-[[2'-(1H-tetrazol-5-yl)[1,1-biphenyl]-4-yl]methyl]-6H-pyrrolo[2,3-d]pyrimidin-6-one and the pharmaceutically acceptable salts thereof;

5,7-dihydro-2-methyl-7-[[2'-(1H-tetrazol-5-yl)[1,1-biphenyl]-4-yl]-methyl]-4-(trifluoromethyl)-6H-pyrrolo[2,3-d]pyrimidin-6-one and the pharmaceutically acceptable salts thereof;

2,4-dimethyl-5,6,8-trihydro-8-[[2'-(1H-tetrazol-5-yl)[1,1-biphenyl]-4-yl]methyl]-7H-pyrido[2,3-d]pyrimidin-7-one and the pharmaceutically acceptable salts thereof;

2-methyl-4-trifluoromethyl-5,6,8-trihydro-8-[[2'-(1H-tetrazol-5-yl)[1,1-biphenyl]-4-yl]methyl]-7H-pyrido[2,3-d]pyrimidin-7-one and the pharmaceutically acceptable salts thereof;

2,4-dimethyl-5,6,8-trihydro-8-[[6-[2-(1H-tetrazol-5-yl)phenyl]-3-pyridinyl]methyl]-7H-pyrido[2,3-d]pyrimidin-7-one and the pharmaceutically acceptable salts thereof;

2-methyl-4-trifluoromethyl-5,6,8-trihydro-8-[[6-[2-(1H-tetrazol-5-yl)phenyl]-3-pyridinyl]methyl]-7H-pyrido[2,3-d]pyrimidin-7-one and the pharmaceutically acceptable salts thereof;

2,4-dimethyl-5,6,8-trihydro-8-[[5-[2-(1H-tetrazol-5-yl)phenyl]-2-pyridinyl]methyl]-7H-pyrido[2,3-d]pyrimidin-7-one and the pharmaceutically acceptable salts thereof;

2,4,6-trimethyl-5,6,8-trihydro-8-[[2'-(1H-tetrazol-5-yl)[1,1-biphenyl]-4-yl]methyl]-7H-pyrido[2,3-d]pyrimidin-7-one and the pharmaceutically acceptable salts thereof;

2,4-dimethyl-8-[[2'-(1H-tetrazol-5-yl)[1,1-biphenyl]-4-yl]methyl]-7H-pyrido[2,3-d]pyrimidin-7-one and the pharmaceutically acceptable salts thereof.

PROCESS

The compounds of the present invention are prepared according to the general sequence of reactions outlined in the Schemes below:

Scheme I

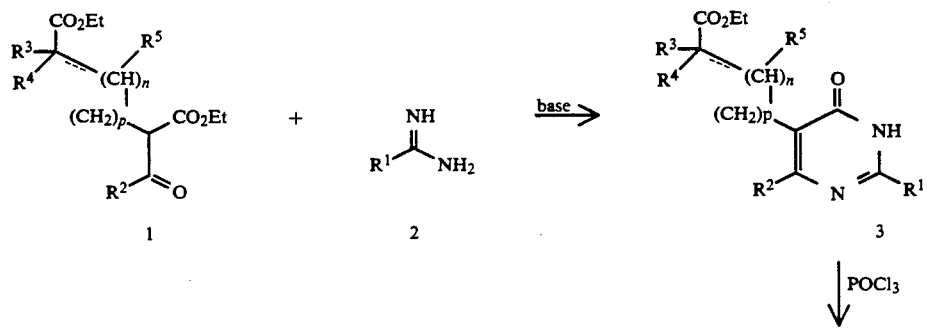

-continued
Scheme I

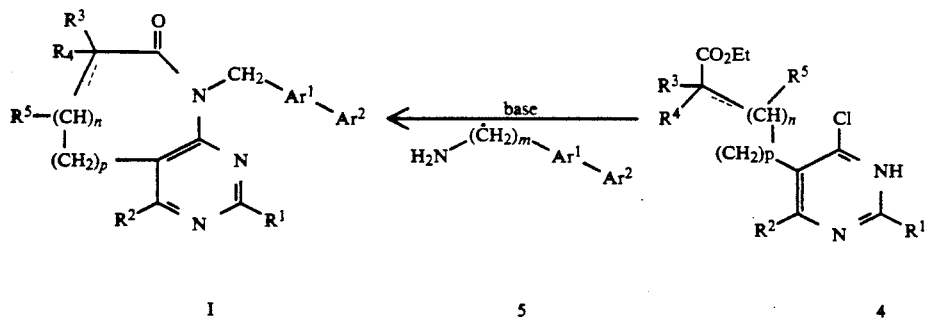

wherein $R^1$, $R^2$, $R^3$, $R^4$, $R^5$, n, m, p, $Ar^1$, and $Ar^2$ are as defined above.

Thus a b-keto ester 1 (Scheme I) is condensed with an amidine 2 in the presence of a base such as sodium ethoxide in an alcoholic solvent such as ethanol at temperatures ranging from ambient to reflux to yield a pyrimidone 3. Treatment of a pyrimidone 3 with phosphorus oxychloride under reflux gives a chloropyrimidine 4. The reaction of 4 with the amine 5 in the presence of an organic base such as triethylamine or an inorganic base such as potassium carbonate in a polar solvent such as ethanol, butanol, or dimethylsulfoxide at temperatures ranging from ambient to reflux yields the target pyrimidines I. The amine 5 is prepared by the palladium catalyzed cross-coupling of an arylstannane or an arylboronic acid with an aryl bromide or an aryl iodide, and subsequent functionalization to an amine.

An alternative process for the production of the compounds of the present invention is set forth in Scheme II.

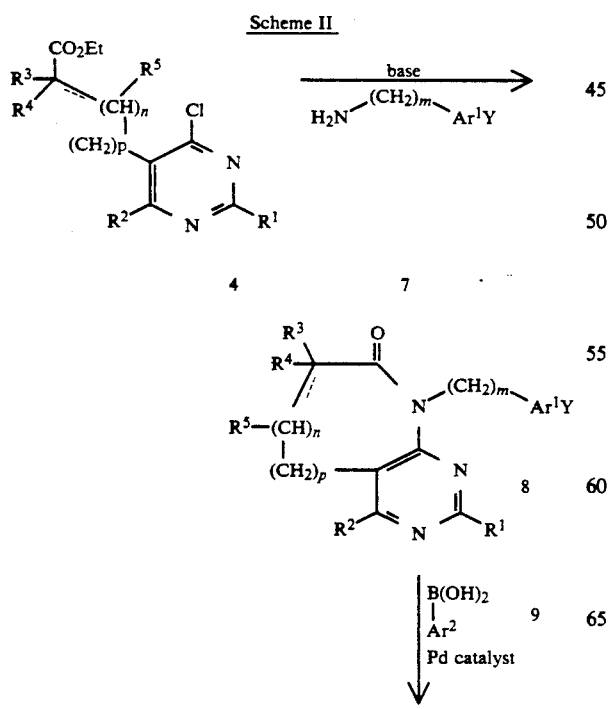

-continued
Scheme II

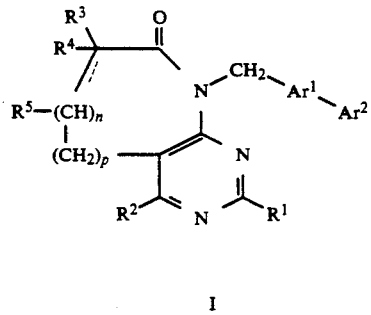

wherein $R^1$, $R^2$, $R^3$, $R^4$, $R^5$, n, m, p, $Ar^1$, and $Ar^2$ are as defined above, and Y is a para-bromo or para-iodo group.

Thus the chloropyrimidine 4 (Scheme II) is treated with an amine 7 in the presence of an inorganic base such as sodium bicarbonate in an alcoholic solvent such as ethanol or n-butanol at temperatures ranging from 80° C. to 150° C. to give the bicyclic compound 8. The reaction of 8 with the arylboronic acid 9 in the presence of a palladium catalyst in a solvent such as DMF or toluene yields the target pyrimidines I. In the case where the substituent on $Ar^2$ is a nitrile, it can be converted to a tetrazole under standard conditions utilizing an azide reagent.

The arylboronic acid 9 is prepared as shown in Scheme III.

Scheme III $$Ar^2-Br \xrightarrow[\text{2) } H^+]{\text{1) Mg, B(OR}^7)_3} Ar^2-B(OH)_2$$

10                                              9 wherein $Ar^2$ is as defined above and $R^7$ is lower alkyl.

Thus the aryl bromide 10 is treated with Mg and a trialkyl borate in an aprotic solvent such as THF. Acidic hydrolysis gives the boronic acid 9.

An alternative process for the production of the compounds of the present invention is set forth in Scheme II.

Scheme IV

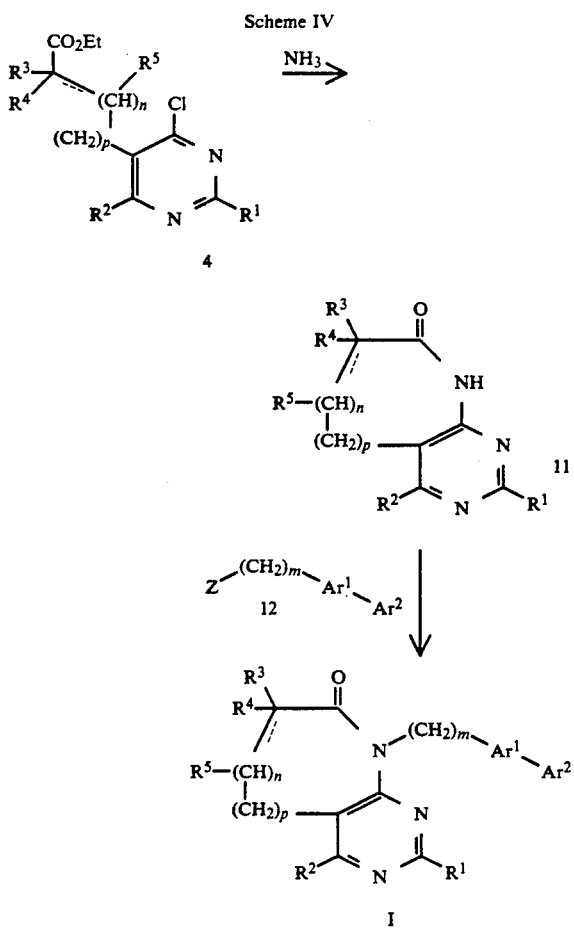

wherein R¹, R², R³, R⁴, n, m, Ar¹, and Ar² are as defined above, and Z is a halogen.

Thus the chloropyrimidine 4 is converted to the bicyclic compound 11 by treatment with ammonia in an alcoholic solvent such as ethanol at temperatures ranging from 100° C. to 150° C. Alkylation of 11 by the biaryl compound 12 is achieved in the presence of a base such as NaH in a solvent such as DMF or THF to give the pyrimidines I. In the case where the substituent on Ar² is a nitrile, it can be converted to a tetrazole by standard conditions utilizing an azide reagent. The biaryl compound 12 is prepared by the palladium catalyzed cross-coupling of an arylstannane or an arylboronic acid with an aryl bromide or an aryl iodide.

When X above is tetrazole, the preferred protecting groups for said tetrazole are those where R⁶ is tert-butyl, tri-n-butylstannyl, or triphenylmethyl. The above groups may be optimally removed by acidic or basic hydrolysis, or catalytic hydrogenation as described by T. Greene, *Protective Groups in Organic Synthesis*, Wiley-Interscience (1980).

The compounds of this invention may also form salts with inorganic or organic acids and bases. Any pharmaceutically acceptable salts of these compounds are within the scope of this invention. These salts may be, but are not limited to, ammonium salts, alkali metal salts such as sodium and potassium, alkaline earth metal salts such as calcium, dicyclohexylamine salts, TRIS salts, and salts of amino acids. Salts with HCl, HBr, maleic acid, fumaric acid may also be formed. The compounds of this invention may also be converted to N-oxides by treatment with hydrogen peroxide by conventional means.

The present invention also provides a pharmaceutical composition which comprises a compound of this invention and a pharmaceutically acceptable carrier. In particular, the present invention provides an anti-hypertensive pharmaceutical composition which comprises an antihypertensive effective amount of a compound of this invention and a pharmaceutically acceptable carrier.

The compositions are preferably adapted for oral administration. However, they may be adapted for other modes of administration, for example parenteral administration for patients suffering from heart failure.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 1 to 50 mg. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day. The compounds may also be administered in a parenteral dosing form.

The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics, b-blocking agents or ACE inhibitors.

The present invention further provides a compound of the invention for use as an active therapeutic substance. Compounds described in this invention are of particular use in the treatment of hypertension.

The present invention further provides a method of treating hypertension in mammals including man, which comprises administering to the aflicted mammal an antihypertensive effective amount of a compound or a pharmaceutical composition of the invention.

The high affinity of the compounds for the angiotensin II receptor was established using a rat adrenal receptor binding assay, measuring the displacement of radiolabeled angiotensin II from the receptor, described as follows: Membrane preparation: 1. Anesthetize male Sprague-Dawley rats, 300–400 g body weight, with $CO_2$ and sacrifice by cervical dislocation. 2. Dissect adrenal glands and keep in ice-cold sucrose buffer (0.2M sucrose, 1 mM EDTA, 10 mM Trizma base, pH=7.2). 3. Remove medulla by squashing. Mince the cortex, rinse and homogenize in a chilled ground glass tissue grinder with 15 mL sucrose buffer. 4. Centrifuge at 3000×g for 10 min. (Sorvall RCSC centrifuge, SS34 rotor 6200 rpm). Decant supernatant through gauze. 5. Centrifuge combined supernatants at 12000×g for 13 min. (Beckman ultracentrifuge, 80Ti rotor, 13000 rpm). 6. Centrifuge the supernatant from step 5 at 102000×g for 60 min. (Beckman ultracentrifuge, 80Ti rotor, 38200 rpm). All steps are carried out at 4° C. 7. Resuspend the pellet in 0.5 mL assay buffer (50 mM Tris HCl, 5 mM $MgCl_2$, 0.2% BSA (protease-free), pH=7.4, 25° C.). 8. Store on ice. 9. Determine membrane protein by Lowry or Bradford assay with BSA as standard. Binding assay: (The assay is performed in triplicate, in 12×75 mm plastic test tubes or in a 96-well plate (final volume of 0.25 mL). 1. Add 140 mL assay buffer. 2. Add 10 mL cold A II (to give final concentrations of $10^{-10}$–$10^{-7}$M for standard curve and $10^{-4}$M for nonspecific binding), compounds (e.g., for final concentrations of 25 and 100 mM or 1 mM, 10 nM and 100 nM) in 50% DMSO, or 50% DMSO as a control. 3. Add 50 mL membrane suspension (e.g., 10 mg protein). 4. Preincubate for 30 min at 25° C. Add 50 mL $^{125}$I-A II which has been prepared as shown below (final concentration=1 nM). 6. Incubate for 35 min at 25° C. 7. Stop the incubation by adding 1 mL ice-cold buffer (assay buffer without BSA). Filter with GF/C filters on cell harvester (filters are presoaked in the assay buffer containing 1% polyethyleneimine). 9. Rinse assay tubes 3× with 5 mL cold buffer (assay buffer without BSA). 10. Cut and deposit the filter discs into test tubes and count on gamma counter for 1 min. Preparation of $^{125}$I-A II: Adjust the specific activity of $^{125}$I-A II purchased from New England Nuclear to 500 mCi/nmole by adding cold A II in water. I. Calculate the quantities of hot A II and the cold A II needed and make the dilution. Aliquot, seal tight, and store frozen until needed. 2. Calculate the concentration of the total A II (hot+cold) after dilution. 3. On the day of assay, thaw the frozen aliquot and adjust the volume to give a concentration of 5 pmole/mL (or 0.25 pmole/50 mL) with assay buffer (+protease-free BSA). For final concentration of 1 nM $^{125}$I-A II in the assay, add 50 ml (or 0.25 pmole) per test tube to a final volume of 250 mL. The results of these binding assays are reported as the inhibitory concentration of the test compound necessary to achieve fifty percent displacement of radiolabeled A II from its receptor ($IC_{50}$), or the percent displacement of binding of A II at its receptor at $10^{-8}$M concentration of test compound (% I). All the examples cited in this invention displayed significant inhibition of A II binding in this assay. Typically these compounds displayed an $IC_{50}$ in this assay of less than or equal to 50 mM.

In accordance with their ability to antagonize angiotensin II, the compounds of this invention show antihypertensive action in the following A II-infused rat model. Procedure: Rats are anesthetized with Dial-Urethane (0.60 mL/kg, ip) and the trachea cannulated with PE 240. Either one femoral artery and both femoral veins or the carotid artery and the corresponding jugular vein are cannulated with PE 50. If the jugular vein is cannulated, two cannulas are placed in the one vein. The initial portion of the duodenum (just distal to the stomach) is cannulated with PE 50 via a small midline incision. Arterial pressure and heart rate are measured from the arterial cannula. Ten to 15 min are allowed following surgery for stabilization of arterial pressure. Ganglion blockade is then produced by intravenous administration of mecamylamine at 3 mg/kg (1 mL/kg of a 3 mg/mL solution). Ganglion blockade causes a fall in arterial pressure of about 50 mmHg. Mecamylamine is given every 90 min throughout the remainder of the experiment. An A II infusion is then begun into the other venous cannula at 0.25 mg/kg min (at 9.6 mL/min). The A II infusion returns arterial pressure to or slightly above the control level. Once arterial pressure has stabilized with the A II infusion, baseline values for mean arterial pressure (MAP) and heart rate are taken. The test compound, suspended in methyl cellulose, is then administered via the duodenal cannula at 0.1, 3 or, 30 mg/kg in a volume of 1 mL/kg. Mean arterial pressure and heart rate values are tabulated at 15, 30, 60, 90, 120, 150, 180, 210, and 240 min after administration of the test compound. For example, the product of Example 1 administered at 3 mg/kg id lowered the A II dependent blood pressure by an average of 41% four hours post-administration.

As illustrated above the compounds of this invention are effective A II antagonists and therefore are useful for treating hypertension. They are also of value in the management of acute and chronic congestive heart failure, primary and secondary pulmonary hyperaldosteronism, secondary hyperaldosteronism, primary and secondary pulmonary hypertension, hypertension associated with oral contraceptive use, vascular disorders such as migraine, Raynaud's disease, luminal hyperplasia and the atherosclerotic process, renal diseases or renal complications of other diseases or therapies such as proteinuria, glomerulonephritis, glomerular sclerosis, scleroderma, diabetic nephropathy, end stage renal disease, renal transplant therapy and others. These compounds will also be useful in the treatment of left ventricular dysfunction, diabetic retinopathy, Alzheimers disease, in the enhancement of cognition, in treatment of elevated intraoccular pressure, and in the enhancement of retinal blood flow. These compounds will also be useful as antidepressants and anxiolytics and in the prevention or treatment of restenosis following angioplasty. The application of the compounds of this invention for these and similar disorders will be apparent to those skilled in the art.

Specific procedures are described in the following experimental examples. These examples are given to illustrate the invention and should not be construed as limiting the invention set forth in the appended claims.

EXAMPLES

EXAMPLE 1

2,4-Dimethyl-5,7-dihydro-7-[[2'-(1H-tetrazol-5-yl)[1,1-biphenyl]-4-yl]methyl]-6H-pyrrolo[2,3-d]pyrimidin-6-one Step 1) Ethyl (2,6-Dimethyl-3H-pyrimidin-4-on-5-yl)acetate A mixture of NaOEt (0.069 mol) in EtOH (prepared from 1.6 g of Na in 100 mL of EtOH), acetamidine hydrochloride (6.5 g, 0.069 mol), and diethyl 2-acetylsuccinate (15.0 g, 0.069 mol) was heated under reflux for 16 h. The mixture was concentrated, taken up in water (50 mL), and acidified with 2N HCl (12 mL). The aqueous mixture was extracted with $CH_2Cl_2$, and the extracts were dried ($MgSO_4$) and concentrated. Trituration with ether gave 3.9 g (27%) of product as a white solid, mp 175°–177° C.

$^1$H NMR (DMSO-$d_6$): d 1.10 (t, 3H), 2.15 (s, 3H), 2.25 (s, 3H), 3.20 (s, 2H), 4.05 (q, 2H), 12.20 (br s, 1H).

Anal. calcd for $C_{10}H_{14}N_2O_3$: C, 57.13; H, 6.71; N, 13.32. Found: C, 57.10; H, 6.63; N, 13.25.

Step 2) Ethyl (4-Chloro-2,6-dimethylpyrimidin-5-yl)acetate

A mixture of ethyl (2,6-dimethyl-3H-pyrimidin-4-on-5-yl)acetate (1.13 g, 5.4 mmol), phosphorus oxychloride (10 mL), and N,N-dimethylaniline (1.3 mL, 10.3 mmol) was heated under reflux for 3.5 h. The reaction mixture was concentrated, poured onto ice, and the resulting mixture was extracted with ether. The combined extracts were washed with water, dried ($MgSO_4$), and concentrated to give 1.2 g (98%) of product as a yellow oil.

¹H NMR (DMSO-d₆): d 1.20 (t, 3H), 2.20 (s, 3H), 2.60 (s, 3H), 3.80 (s, 2H), 4.10 (q, 2H).

Step 3) 2,4-Dimethyl-5,7-dihydro-7-[[2'-(1H-tetrazol-5-yl)[1,1-biphenyl]-4-yl]methyl]-6H-pyrrolo[2,3-d]pyrimidin-6-one A mixture of ethyl (4-chloro-2,6-dimethylpyrimidin-5-yl)acetate (0.55 g, 2.4 mmol), 5-[(4'-aminomethyl)[1,1-biphen-2-yl]]-1H-tetrazole hydrochloride (0.69 g, 2.4 mmol), triethylamine (0.73 g, 7.2 mmol), sodium acetate (0.60 g, 7.2 mmol), and EtOH (14 mL) was heated under reflux for 5 days. The mixture was concentrated, taken up in water, and extracted with CHCl₃. The extracts were dried (MgSO₄), concentrated, and the crude product was purified by flash chromatography (10% MeOH/CHCl₃) to give a yellow solid. Trituration with 10% EtOH/Et₂O and recrystallization form EtOH afforded 0.17 g (17%) of product as a white solid, mp 228°–229° C.

¹H NMR (DMSO-d₆): d 2.29 (s, 3H), 2.47 (s, 3H), 3.67 (s, 2H), 4.83 (s, 2H), 7.05 (d, J=8.1 Hz, 2H), 7.24 (d, J=8.1 Hz, 2H), 7.57 (m, 2H), 7.63 (m, 2H).

Anal. calcd for $C_{22}H_{19}N_7O$: C, 66.48; H, 4.82; N, 24.67. Found: C, 66.09; H, 4.84; N, not determined.

EXAMPLE 2

5,7-Dihydro-2-methyl-7-[[2'-(1H-tetrazol-5-yl)[1,1-biphenyl]-4-yl]methyl]-4-(trifluoromethyl)-6H-pyrrolo[2,3-d]pyrimidin-6-one Step 1) Ethyl (2-Methyl-6-trifluoromethyl-3H-pyrimidin-4-on-5-yl)acetate A mixture of NaOEt (0.074 mol) in EtOH (prepared from 1.7 g of Na and 75 mL of EtOH), acetamidine hydrochloride (3.5 g, 0.037 mol), and diethyl 2-trifluoroacetylsuccinate (10.0 g, 0.037 mol) was heated under reflux for 20 h. The mixture was concentrated, taken up in water, acidified to pH 4 with conc. HCl, and extracted with EtOAc. The extracts were washed with brine, dried (MgSO₄), and concentrated to give an oily solid. Trituration with ether/hexane gave 2.63 g (27%) of product as a white solid. An analytical sample was recrystallized from ether/hexane, mp 108°–110° C.

¹H NMR (DMSO-d₆): d 1.25 (t, J=7.2 Hz, 3H), 2.51 (s, 3H), 3.72 (s, 2H), 4.17 (q, J=7.2 Hz, 2H), 13.25 (br s, 1H).

Anal. calcd for $C_{10}H_{11}F_3N_2O_3$: C, 45.46; H, 4.20; N, 10.60. Found: C, 45.43; H, 4.18; N, 10.53.

Step 2) Ethyl (4-Chloro-2-methyl-6-trifluoromethyl-pyrimidin-5-yl)acetate

A solution of ethyl (2-methyl-6-trifluoromethyl-3H-pyrimidin-4-on-5-yl)acetate (2.50 g, 9.46 mmol), N,N-dimethylaniline (3 drops), and phosphorus oxychloride (35 mL) was heated under reflux for 4.5 h. The mixture was concentrated, cooled, and ice water was added. Solid KOH was added to neutralize the mixture and it was extracted with ether. The combined extracts were washed with brine, dried (MgSO₄), and concentrated to give 2.61 g (98%) of product as a yellow oil. ¹H NMR (DMSO-d₆): d 1.24 (t, J=0.7 Hz, 3H), 2.77 (s, 3H), 3.93 (s, 2H), 4.19 (q, J=7.0 Hz, 2H).

Step 3) 5,7-Dihydro-2-methyl-7-[[2'-(1H-tetrazol-5-yl)[1,1-biphenyl]-4-yl]methyl]-4-(trifluoromethyl)-6H-pyrrolo[2,3-d]pyrimidin-6-one A mixture of ethyl (4-chloro-2-methyl-6-trifluoromethylpyrimidin-5-yl)acetate (848 mg, 3.00 mmol), 5-[(4'-aminomethyl)[1,1-biphen-2-yl]]-1H-tetrazole hydrochloride (863 mg, 3.00 mmol), triethylamine (1.25 mL, 9.00 mmol), sodium acetate (738 mg, 9.00 mmol), and EtOH (10 mL) was heated under reflux for 16 h. The mixture was concentrated, taken up in 1N NaOH, and extracted with ether. The aqueous phase was acidified to pH 3 with conc. HCl and the dark brown precipitate was collected by filtration. Purification by flash chromatography (twice; 5–10% MeOH/CH₂Cl₂) gave a brown foam. Crystallization from ether/hexane gave 109 mg (8%) of product as a white solid, mp 195°–197° C.

¹H NMR (DMSO-d₆): d 2.59 (s, 3H), 3.92 (s, 2H), 4.90 (s, 2H), 7.05 (d, J=8.1 Hz, 2H), 7.28 (d, J=8.1 Hz, 2H), 7.52 (d, J=6.2 Hz, 1H), 7.57 (d, J=7.4 Hz, 1H), 7.66 (m, 2H).

IR (KBr, cm⁻¹): 1750 (C=O).

Anal. calcd for $C_{22}H_{16}F_3N_7O$: C, 58.54; H, 3.57; N, 21.72. Found: C, 58.58; H, 3.71; N, 21.44.

EXAMPLE 3

2,4-Dimethyl-5,6,8-trihydro-8-[[2'-(1H-tetrazol-5-yl)[1,1-biphenyl]-4-yl]methyl]-7H-pyrido[2,3-d]pyrimidin-7-one Step 1) Ethyl 3-(2,6-Dimethyl-3H-pyrimidin-4-on-5-yl)propionate A mixture of NaOEt (0.069 mol) in EtOH (prepared from 1.6 g of Na and 35 mL of EtOH), acetamidine hydrochloride (3.3 g, 0.035 mol), and diethyl acetylglutarate (8.0 g, 0.035 mol) was heated under reflux for 22 h. The mixture was concentrated, taken up in water, acidified to pH 4 with conc. HCl, and extracted with EtOAc. The extracts were washed with brine, dried (MgSO₄), and concentrated. Trituration with hexane gave 4.0 g (51%) of product as a white solid. An analytical sample was crystallized from ether/hexane, mp 114°–116° C.

¹H NMR (DMSO-d₆): d 1.22 (t, J=7.2 Hz, 3H), 2.33 (s, 3H), 2.40 (s, 3H), 2.54 (t, J=8.0 Hz, 2H), 2.81 (t, J=8.0 Hz, 2H), 4.10 (q, J=7.2 Hz, 2H).

Anal. calcd for $C_{11}H_{16}N_2O_3$: C, 58.91; H, 7.19; N, 12.49. Found: C, 59.18; H, 7.25; N, 12.20.

Step 2) Ethyl 3-(4-Chloro-2,6-dimethylpyrimidin-5-yl)propionate

A mixture of ethyl 3-(2,6-dimethyl-3H-pyrimidin-4-on-5-yl)propionate (3.87 g, 0.017 mol), phosphorus oxychloride (40 mL), and N,N-dimethylaniline (10 drops) was heated under reflux for 2 h. The mixture was concentrated, cooled, and ice water was added. Solid KOH was added to bring the pH to 6 and the mixture was extracted with ether. The extracts were dried (MgSO₄) and concentrated to give 2.95 g (72%) of product as a brown oil.

¹H NMR (DMSO-d₆): d 1.24 (t, J=7.2 Hz, 3H), 2.54 (s, 3H), 2.56 (t, J=8.1 Hz, 2H), 2.81 (s, 3H), 3.04 (t, J=8.1 Hz, 2H), 4.14 (q, J=7.2 Hz, 2H).

Step 3) 2,4-Dimethyl-5,6,8-trihydro-8-[[2'-(1H-tetrazol-5-yl)[1,1-biphenyl]-4-yl]methyl]-7H-pyrido[2,3-d]pyrimidin-7-one A mixture of ethyl 3-(4-chloro-2,6-dimethylpyrimidin-5-yl)propionate (1.27 g, 5.21 mmol), 5-[(4'-aminomethyl)[1,1-biphen-2-yl]]-1H-tetrazole hydrochloride (1.50 g, 5.21 mmol), triethylamine (2.2 mL, 15.64 mmol), sodium acetate (1.28 g, 15.64 mmol), and EtOH (20 mL) was heated under reflux for 5 days. The mixture was cooled and filtered to remove insoluble material. The filtrate was acidified to pH 4 with methanolic HCl and concentrated. Purification by flash chromatography (10% MeOH/CH₂Cl₂) and crystallization from EtOH/ether gave 91 mg of product as a white solid, mp 197°–199° C.

¹H NMR (DMSO-d₆): d 2.35 (s, 3H), 2.42 (s, 3H), 2.72 (t, J=7.2 Hz, 2H), 2.87 (t, J=7.2 Hz, 2H), 5.17 (s, 2H), 6.99 (d, J=8.2 Hz, 2H), 7.18 (d, J=8.2 Hz, 2H), 7.54 (m, 2H), 7.65 (m, 2H).

IR (KBr, cm⁻¹): 1710 (C=O).

Anal. calcd for $C_{23}H_{21}N_7O$: C, 67.14; H, 5.14; N, 23.83. Found: C, 67.38; H, 5.39; N, 24.19.

The compound 2,4-dimethyl-5,6,8-trihydro-8-[[2'-(1H-tetrazol-5-yl)[1,1-biphenyl]-4-yl]methyl]-7H-pyrido[2,3-d]pyrimidin-7-one may also be prepared by the following alternate process, set forth in Scheme II.

Step 1) 2,4-Dimethyl-5,6,8-trihydro-8-[(4-bromophenyl)methyl]-7H-pyrido[2,3-d]pyrimidin-7-one A mixture of ethyl 3-(4-chloro-2,6-dimethylpyrimidin-5-yl)propionate (8.4 g, 0.035 mol), 4-bromobenzylamine hydrochloride (8.5 g, 0.038 mol), NaHCO₃ (5.8 g, 0.070 mol), and nBuOH (75 mL) was heated under reflux for 48 h. The mixture was diluted with EtOAc (30 mL) and washed with water (100 mL), 10% aqueous HOAc (50 mL), water (100 mL), saturated aqueous NaHCO₃ (2×100 mL), dried (MgSO₄), and concentrated to give a yellow solid. Trituration with hexane (50 mL) gave 8.3 g (69%) of product as an off-white solid, mp 123°-124° C.

¹H NMR (DMSO-d₆): d 2.34 (s, 3H), 2.42 (s, 3H), 2.71 (t, J=7.9 Hz, 2H), 2.86 (t, J=7.9 Hz, 2H), 5.13 (s, 2H), 7.22 (d, J=8.3 Hz, 2H), 7.44 (d, J=8.3 Hz, 2H).

Step 2) 5-(2-Bromophenyl)-1H-tetrazole

A mixture of 2-bromobenzonitrile (10.0 g, 0.055 mol), sodium azide (3.9 g, 0.060 mol), ammonium chloride (3.2 g, 0.060 mol), and DMF (90 mL) was heated at 100° C. for 18 h. The mixture was concentrated, taken up in water, and made basic (pH 9) with 1N KOH. The aqueous mixture was extracted with ether (discarded) and acidified with 2N HCl. The precipitate was collected by filtration to give 9.1 g (73%) of product as an off-white solid, mp 179°-181° C. ¹H NMR (DMSO-d₆): d 7.56 (m, 2H), 7.69 (dd, J=7.0 Hz, 2.1 Hz, 1H), 7.86 (dd, J=7.6 Hz, 1.3 Hz, 1H).

Step 3) 1-tert-Butyl-5-(2-bromophenyl)-1H-tetrazole

To a solution of 5-(2-bromophenyl)-1H-tetrazole (7.9 g, 0.035 mol) in trifluoroacetic acid (35 mL) was added tBuOH (5.2 g, 0.070 mol) and H₂SO₄ (1.0 mL, 0.0175 mol). After 18 h, the solution was concentrated and the residue was taken up in EtOAc. The mixture was washed with water, 2.5N NaOH, water, dried (MgSO₄), and concentrated. Purification by flash chromatography (20% EtOAc/hexane) gave 6.6 g (67%) of product as a pale yellow oil. ¹H NMR (DMSO-d₆): d 1.74 (s, 9H), 7.55 (m, 2H), 8.06 (m, 2H).

Step 4) 2-[(1-tert-Butyl)-1H-tetrazol-5-yl]phenylboronic acid

To dry Mg turnings (76 mg, 3.13 mmol) in THF (1 mL) was added a solution of 1-tert-butyl-5-(2-bromophenyl)-1H-tetrazole (733 mg, 2.61 mmol) in THF (1.5 mL). 1,2-Dibromoethane (20 mL) was added and the mixture was warmed slightly with a heat gun. After 5 min, triisopropyl borate (564 mg, 3.00 mmol) was added and the mixture was stirred at room temperature for 23 h. Ice and 0.5N HCl (7 mL) were added and the mixture was stirred for 5 min. The mixture was extracted with ether, and the combined extracts were extracted with 1N KOH (10 mL). The aqueous extracts were filtered and acidified to pH 3 with 2N HCl. The precipitate was collected by filtration to give 306 mg (48%) of product as an off-white solid, mp 112°-115° C. ¹H NMR (DMSO-d₆): d 1.72 (s, 9H), 7.46 (m, 2H), 7.90 (m, 2H).

Step 5) 2,4-Dimethyl-5,6,8-trihydro-8-[[2'-(1-tert-butyl-1H-tetrazol-5-yl)[1,1-biphenyl]-4-yl]methyl]-7H-pyrido[2,3-d]pyrimidin-7-one A mixture of 2,4-dimethyl-5,6,8-trihydro-8-[(4-bromophenyl)methyl]-7H-pyrido[2,3-d]pyrimidin-7-one (1.08 g, 3.43 mmol), 2-[(1-tert-butyl)-1H-tetrazol-5-yl]phenylboronic acid (844 mg, 3.12 mmol), triethylamine (1.30 mL, 9.36 mmol), tetrakis(triphenylphosphine)palladium (108 mg, 0.094 mmol), and DMF (15 mL) was heated at 100° C. for 22 h. The mixture was concentrated, taken up in CHCl₃, and washed with brine. The organic phase was dried (MgSO₄) and concentrated. Purification by flash chromatography (60% EtOAc/hexane) gave 1.05 g (66%) of product as a yellow foam.

¹H NMR (DMSO-d₆): d 2.35 (s, 3H), 2.43 (s, 3H), 2.71 (t, J=7.1 Hz, 2H), 2.85 (t, J=7.1 Hz, 2H), 5.18 (s, 2H), 6.97 (d, J=8.2 Hz, 2H), 7.18 (d, J=8.2 Hz, 2H), 7.44 (dd, J=7.3 Hz, 1.3 Hz, 1H), 7.55 (m, 2H), 7.76 (dd, J=7.5 Hz, 1.3 Hz, 1H).

Step 6) 2,4-Dimethyl-5,6,8-trihydro-8-[[2'-(1H-tetrazol-5-yl)[1,1-biphenyl]-4-yl]methyl]-7H-pyrido[2,3-d]pyrimidin-7-one A mixture of 2,4-dimethyl-5,6,8-trihydro-8-[[2'-(1-tert-butyl-1H-tetrazol-5-yl)[1,1-biphenyl]-4-yl]methyl]-7H-pyrido[2,3-d]pyrimidin-7-one (200 mg, 0.428 mmol), methanesulfonic acid (280 mL, 4.28 mmol), and toluene (4 mL) was heated under reflux for 18 h. The mixture was concentrated, and water (2 mL) and 1N KOH (4.5 mL) were added to give a solution of pH 8. The mixture was extracted with EtOAc to remove unreacted starting material, and the aqueous phase was acidified to pH 5 with 1N HCl to give a gummy precipitate. The precipitate was extracted into EtOAc, and the solution was dried (MgSO₄) and concentrated to give a colorless oil. Trituration with acetone/ether gave 70 mg (40%) of product as a white solid, mp 197°-198° C.

¹H NMR (DMSO-d₆): d 2.35 (s, 3H), 2.42 (s, 3H), 2.72 (t, J=7.2 Hz, 2H), 2.87 (t, J=7.2 Hz, 2H), 5.17 (s, 2H), 6.99 (d, J=8.2 Hz, 2H), 7.18 (d, J=8.2 Hz, 2H), 7.54 (m, 2H), 7.65 (m, 2H).

IR (KBr, cm⁻¹): 1710 (C=O).

EXAMPLE 4

2-Methyl-4-trifluoromethyl-5,6,8-trihydro-8-[[2'-(1H-tetrazol-5-yl)[1,1-biphenyl]-4-yl]methyl]-7H-pyrido[2,3-d]pyrimidin-7-one Step 1) Diethyl Trifluoroacetylglutarate To a solution of NaOEt (0.217 mol) in EtOH (prepared from 5.0 g of Na and 220 mL of EtOH) was added ethyl triflouroacetoacetate (40.0 g, 0.217 mol). After 10 min, ethyl 3-bromopropionate (35.0 g, 0.194 mol) was added and the mixture was heated under reflux for 24 h. The reaction mixture was concentrated, taken up in ether, and washed with water. The ether layers were dried (MgSO₄) and concentrated to give 50 g of a yellow oil. Distillation (100°-110° C./25 mm) gave 14.0 g (23%) of product as a colorless oil.

¹H NMR (DMSO-d₆): d 1.20 (m, 6H), 2.93 (t, J=6.4 Hz, 2H), 3.62 (t, J=6.4 Hz, 2H), 4.13 (m, 5H).

Step 2) Ethyl 3-(2-Methyl-6-trifluoromethyl-3H-pyrimidin-4-on-5-yl)propionate

To a solution of NaOEt (0.026 mol) in EtOH (prepared from 0.60 g of Na and 30 mL of EtOH) was added diethyl trifluoroacetylglutarate (3.70 g, 0.013 mol) and acetamidine hydrochloride (1.23 g, 0.013 mol). The reaction mixture was heated under reflux for 18 h, concentrated, and taken up in water. The mixture was acidified to pH 4 with 2N HCl and extracted with CH$_2$Cl$_2$. The extracts were dried (MgSO$_4$) and concentrated to give a yellow solid. Trituration with hexane gave 0.87 g of product as a white solid.

$^1$H NMR (DMSO-d$_6$): d 1.16 (t, J=7.0 Hz, 3H), 2.35 (s, 3H), 2.45 (t, J=6.4 Hz, 2H), 2.70 (t, J=6.4 Hz, 2H), 4.06 (q, J=7.0 Hz, 2H).

Step 3) Ethyl 3-(4-Chloro-2-methyl-6-trifluoromethylpyrimidin-5-yl)propionate

A mixture of ethyl 3-(2-methyl-6-trifluoromethyl-3H-pyrimidin-4-on-5-yl)propionate (0.61 g, 2.20 mmol), N,N-diethylaniline (0.33 g, 2.2 mmol), and POCl$_3$ (8 mL) was heated under reflux for 2 h. The mixture was concentrated, poured onto ice, and extracted with ether. The combined extracts were dried (MgSO$_4$) and concentrated to give 0.65 g of product as a brown oil.

$^1$H NMR (DMSO-d$_6$): d 1.18 (t, J=7.0 Hz, 3H), 2.56 (t, J=8.5 Hz, 2H), 2.67 (s, 3H), 3.06 (t, J=8.5 Hz, 2H), 4.10 (m, 2H).

Step 4) 2-Methyl-4-trifluoromethyl-5,6,8-trihydro-8-[[2'-(1H-tetrazol-5-yl)[1,1-biphenyl]-4-yl]methyl]-7H-pyrido[2,3-d]pyrimidin-7-one A mixture of ethyl 3-(4-chloro-2-methyl-6-trifluoromethylpyrimidin-5-yl)propionate (1.30 g, 4.40 mmol), 5-[(4'-aminomethyl)[1,1-biphen-2-yl]]-1H-tetrazole hydrochloride (1.26 g, 4.40 mmol), sodium acetate (1.08 g, 13.20 mmol), and triethylamine (1.33 g, 13.20 mmol) in nBuOH (25 mL) was heated under reflux for 24 h. The mixture was concentrated and partitioned between CHCl$_3$ and water. The layers were separated and the organic phase was washed with water, dried (MgSO$_4$), and concentrated to give a yellow oil. Purification by flash chromatography (7% MeOH/CH$_2$Cl$_2$) and recrystallization from acetone/ether (twice) gave 0.07 g of product as a white solid, mp 219°–220° C.

$^1$H NMR (DMSO-d$_6$): d 2.53 (s, 3H), 2.81 (t, J=7.1 Hz, 2H), 3.07 (t, J=7.1 Hz, 2H), 5.2 (s, 2H), 7.00 (d, J=8.1 Hz, 2H), 7.22 (d, J=8.1 Hz, 2H), 7.56 (m, 2H), 7.65 (m, 2H).

Anal. calcd for C$_{23}$H$_{18}$F$_3$N$_7$O: C, 59.35; H, 3.90; N, 21.07. Found: C, 59.12; H, 3.85; N, 21.29.

EXAMPLE 5

2,4-Dimethyl-5,6,8-trihydro-8-[[6-[2-(1H-tetrazol-5-yl)phenyl]-3-pyridinyl]methyl]-7H-pyrido[2,3-d]pyrimidin-7-one Step 1) 2,4-Dimethyl-5,6,8-trihydro-7H-pyrido[2,3-d]pyrimidin-7-one To a cooled (−78° C.) solution of ethyl 3-(4-chloro-2,6-dimethylpyrimidin-5-yl)propionate (27.1 g, 0.111 mol), prepared as described in Step 2 of Example 3, in EtOH (110 mL) was added liquid NH$_3$ (20 mL). The mixture was heated at 150° C. in a pressure vessel for 12 h and concentrated. Water (20 mL) was added and the mixture was extracted with CH$_2$Cl$_2$. The extracts were dried (MgSO$_4$) and concentrated to give a brown solid. Purification by flash chromatography (2% MeOH/CH$_2$Cl$_2$) and trituration with ether/hexane gave 14.9 g (76%) of product as off-white crystals, mp 167°–168° C.

$^1$H NMR (DMSO-d$_6$): d 2.30 (s, 3H), 2.40 (s, 3H), 2.52 (t, J=7.7 Hz, 2H), 2.80 (t, J=7.7 Hz, 2H), 10.64 (s, 1H). IR (KBr, cm$^{-1}$): 1690.

Anal. calcd for C$_9$H$_{11}$N$_3$O: C, 61.00; H, 6.26; N, 23.71. Found: C, 61.04; H, 6.07; N, 24.10.

Step 2) 2-Bromo-5-hydroxymethylpyridine

To a cooled (0° C.), stirred suspension of 6-bromonicotinic acid (13.8 g, 0.068 mol), prepared according to Campbell, et al. *Aust. J. Chem.* 1971, 24, 277, in THF (20 mL) was added 1.0M BH$_3$ in THF (204 mL, 0.204 mol). The mixture was stirred at room temperature for 3 h, recooled to 0° C., and saturated aqueous K$_2$CO$_3$ and water were added. The mixture was extracted with EtOAc, and the combined extracts were washed with water, dried (MgSO$_4$), and concentrated to give a yellow oil. Purification by flash chromatography (2% MeOH/CH$_2$Cl$_2$) gave 7.5 g (59%) of a yellow solid, mp 49°–51° C.

$^1$H NMR (DMSO-d$_6$): d 4.50 (d, J=5.7 Hz, 2H), 5.40 (t, J=5.7 Hz, 1H), 7.57 (d, J=8.3 Hz, 1H), 7.70 (dd, J=8.3 Hz, 1.5 Hz, 1H), 8.35 (d, J=1.5 Hz, 1H).

Step 3) 2-Bromo-5-(tert-butyldimethylsilyloxy)methylpyridine

To a stirred mixture of 2-bromo-5-hydroxymethylpyridine (4.7 g, 0.023 mol) and triethylamine (3.4 mL, 0.024 mol) in DMF (30 mL) was added tertbutyldimethylsilyl chloride. After 1 h, the mixture was diluted with ether and washed with water. The ether phase was dried (MgSO$_4$) and concentrated to give 6.8 g (97%) of product as a colorless oil.

$^1$H NMR (DMSO-d$_6$): d 0.10 (s, 6H), 0.90 (s, 3H), 4.73 (s, 2H), 7.65 (m, 2H), 8.35 (d, J=1.5 Hz, 1H).

Step 4) [5-(tert-Butyldimethylsilyloxymethyl)pyridin-2-yl]tri-n-butylstannane

To a cooled (−78° C.), stirred solution of 2-bromo-5-(tertbutyldimethylsilyloxy)methylpyridine (6.8 g, 0.022 mol) in THF (60 mL) was added 1.6M nBuLi in hexanes (14.1 mL, 0.022 mol). After 1 h, tri-n-butyltin chloride (6.1 mL, 0.022 mol) was added and stirring was continued for 3 h. Water was added, and the mixture was warmed to room temperature and extracted with ether. The combined extracts were dried (MgSO$_4$) and concentrated to give 11.5 g (100%) of product as a brown oil.

$^1$H NMR (DMSO-d$_6$): d 0.10 (s, 6H), 0.80 (m, 18H), 1.10 (m, 6H), 1.25 (m, 6H), 1.50 (m, 6H), 4.73 (s, 2H), 7.55 (m, 2H), 8.61 (d, J=2.2 Hz, 1H).

Step 5) 2-[5-(tert-Butyldimethylsilyloxymethyl)pyridin-2-yl]benzonitrile

A mixture of [5-(tert-butyldimethylsilyloxymethyl)-pyridin-2-yl]tri-n-butylstannane (11.5 g, 0.022 mol), 2-iodobenzonitrile (5.1 g, 0.022 mol), CuI (0.43 g, 0.002 mol), and bis(triphenylphosphine)palladium(II) chloride (0.80 g, 0.001 mol) in THF (40 mL) was heated under reflux for 48 h. The mixture was diluted with ether and washed with saturated aqueous NH$_4$Cl, aqueous NH$_4$OH, water, and brine, dried (MgSO$_4$), and concentrated to give 4.9 g (67%) of product as a brown oil.

$^1$H NMR (DMSO-d$_6$): d 0.10 (s, 6H), 0.90 (s, 9H), 4.73 (s, 2H), 7.45 (m, 1H), 7.60 (m, 4H), 7.75 (dd, J=7.9 Hz, 2.2 Hz, 1H), 8.50 (d, J=2.2 Hz, 1H).

Step 6) 2-[5-(Hydroxymethyl)pyridin-2-yl]benzonitrile

A mixture of 2-[5-(tert-butyldimethylsilyloxymethyl)pyridin-2-yl]benzonitrile (4.9 g, 0.021 mol) and nBu$_4$NF hydrate (8.1 g, 0.031 mol) in THF (60 mL) was stirred at room temperature for 18 h. The mixture was diluted with EtOAc, washed with water and brine, dried (MgSO$_4$), and concentrated to give 3.5 g (80%) of product as a brown solid, mp 152°–153° C.

$^1$H NMR (DMSO-d$_6$): d 4.61 (d, J=5.6 Hz, 2H), 5.42 (t, J=5.6 Hz, 1H), 7.57 (dd, J=7.3 Hz, 1.5 Hz, 1H), 7.65

(m, 4H), 7.80 (dd, J=7.9 Hz, 2.2 Hz, 1H), 8.52 (d, J=2.2 Hz, 1H).

Step 7) 2-[5-(Chloromethyl)pyridin-2-yl]benzonitrile

To a cooled (0° C.), stirred solution of 2-[5-(hydroxymethyl)pyridin-2-yl]benzonitrile (4.3 g, 0.020 mol) and ZnCl₂ (0.09 g, 0.61 mmol) in p-dioxane (40 mL) was added SOCl₂ (1.50 mL, 0.020 mol) dropwise. The mixture was stirred at room temperature for 18 h, diluted with ether, washed with water and brine, dried (MgSO₄), and concentrated to give 4.30 g (92%) of product as a brown solid, mp 97°-98° C.

¹H NMR (DMSO-d₆): d 4.90 (s, 2H), 7.63 (dd, J=7.7 Hz, 1.3 Hz, 1H), 7.80 (m, 1H), 7.85 (m, 2H), 7.95 (d, J=7.7 Hz, 1H), 8.01 (dd, J=8.0 Hz, 2.2 Hz, 1H), 8.80 (d, J=2.2 Hz, 1H).

Step 8) 2,4-Dimethyl-5,6,8-trihydro-8-[[6-(2-cyanophenyl)-3-pyridinyl]methyl]-7H-pyrido[2,3-d]pyrimidin-7-one To a stirred suspension of NaH (60% dispersion in mineral oil; 0.42 g, 9.18 mmol) in DMF (20 mL) was added 2,4-dimethyl-5,6,8-trihydro-7H-pyrido[2,3-d]pyrimidin-7-one (1.55 g, 8.75 mmol). After 1 h, 2-[5-(chloromethyl)pyridin-2-yl]benzonitrile (2.00 g, 8.75 mmol) was added in several portions. Stirring was continued for 4 h and the mixture was concentrated. Water was added and the mixture was extracted with CH₂Cl₂. The combined extracts were dried (MgSO₄) and concentrated to give 3.20 g (100%) of product as a brown solid, mp 161°-162° C.

¹H NMR (DMSO-d₆): d 2.36 (s, 3H), 2.45 (s, 3H), 2.78 (t, J=7.8 Hz, 2H), 2.87 (t, J=7.8 Hz, 2H), 5.27 (s, 2H), 7.61 (m, 1H), 7.80 (m, 4H), 7.93 (dd, J=7.7 Hz, 1.3 Hz, 1H), 8.70 (d, J=1.3 Hz, 1H).

Step 9) 2,4-Dimethyl-5,6,8-trihydro-8-[[6-[2-(1H-tetrazol-5-yl)phenyl]-3-pyridinyl]methyl]-7H-pyrido[2,3-d]pyrimidin-7-one A mixture of 2,4-dimethyl-5,6,8-trihydro-8-[[6-(2-cyanophenyl)-3-pyridinyl]methyl]-7H-pyrido[2,3-d]pyrimidin-7-one (4.0 g, 10.8 mmol), NaN₃ (0.8 g, 11.9 mmol), and tri-n-butyltin chloride (3.9 g, 11.9 mmol) in xylenes (100 mL) was heated under reflux for 24 h. Another 1.5 equiv. of NaN₃ and tri-n-butyltin chloride were added and heating was continued for 24 h. The reaction mixture was concentrated and 2N HCl was added. The mixture was extracted with ether (discarded) and adjusted to pH 5 with 50% NaOH. The aqueous phase was extracted with CH₂Cl₂, and the extracts were washed with water, dried (MgSO₄), and concentrated. Purification by flash chromatography (5% MeOH/CH₂Cl₂) and recrystallization from EtOH/water gave 2.8 g (63%) of product as a white solid, mp 217°-218° C.

¹H NMR (DMSO-d₆): d 2.35 (s, 3H), 2.44 (s, 3H), 2.73 (t, J=7.8 Hz, 2H), 2.85 (t, J=7.8 Hz, 2H), 5.18 (s, 2H), 7.33 (d, J=8.3 Hz, 1H), 7.65 (m, 5H), 8.36 (s, 1H).

IR (KBr, cm⁻¹): 1690.

Anal. calcd for $C_{22}H_{20}N_8O$: C, 64.07; H, 4.89; N, 27.17 Found: C, 63.87; H, 4.81; N, 27.56.

EXAMPLE 6

2-Methyl-4-trifluoromethyl-5,6,8-trihydro-8-[[6-[2-(1H-tetrazol-5-yl)phenyl]-3-pyridinyl]methyl]-7H-pyrido[2,3-d]pyrimidin-7-one Step 1) 2-Methyl-4-trifluoromethyl-5,6,8-trihydro-7H-pyrido[2,3-d]pyrimidin-7-one A solution of ethyl 3-(4-chloro-2-methyl-6-trifluoromethylpyrimidin-5-yl)propionate (0.50 g, 1.70 mmol), prepared as described in Step 3 of Example 4, in saturated ethanolic ammonia (15 mL) was heated in a sealed tube at 110° C. for 18 h. The mixture was concentrated, taken up in CH₂Cl₂, and washed with water. The organic layer was dried (MgSO₄) and concentrated to give 0.33 g (84%) of product as a white solid, mp 147°-150° C.

¹H NMR (DMSO-d₆): d 2.53 (s, 3H), 2.61 (t, J=7.3 Hz, 2H), 3.01 (t, J=7.3 Hz, 2H), 11.30 (s, 1H).

Step 2) 2-Methyl-4-trifluoromethyl-5,6,8-trihydro-8-[[6-(2-cyanophenyl)-3-pyridinyl]methyl]-7H-pyrido[2,3-d]pyrimidin-7-one To a suspension of NaH (60% dispersion in mineral oil; 33 mg, 1.40 mmol) in DMF was added 2-methyl-4-trifluoromethyl-5,6,8-trihydro-7H-pyrido[2,3-d]pyrimidin-7-one (0.32 g, 1.40 mmol) at room temperature. After 30 min, 2-[5-(chloromethyl)pyridin-2-yl]benzonitrile (0.32 g, 1.40 mmol), prepared as described in Step 7 of Example 5, was added. The mixture was stirred for 42 h, diluted with water, and extracted with CH₂Cl₂. The combined extracts were dried (MgSO₄) and concentrated to give 0.51 g (86%) of product as a yellow foam.

¹H NMR (DMSO-d₆): d 2.58 (s, 3H), 2.86 (t, J=7.6 Hz, 2H), 3.11 (t, J=7.6 Hz, 2H), 5.31 (s, 2H), 7.62 (m, 1H), 7.85 (m, 5H), 8.75 (s, 1H).

Step 3) 2-Methyl-4-trifluoromethyl-5,6,8-trihydro-8-[[6-[2-(1H-tetrazol-5-yl)phenyl]-3-pyridinyl]methyl]-7H-pyrido[2,3-d]pyrimidin-7-one A mixture of 2-methyl-4-trifluoromethyl-5,6,8-trihydro-8-[[6-(2-cyanophenyl)3-pyridinyl]methyl]-7H-pyrido[2,3-d]pyrimidin-7-one (0.50 g, 1.23 mmol), NaN₃ (0.08 g, 1.23 mmol), and tri-n-butyltin chloride (0.40 g, 1.23 mmol) in xylenes (9 mL) was heated under reflux for 48 h. 1N HCl (1.2 mL) was added and the mixture was diluted with CH₂Cl₂, washed with water, dried (MgSO₄), and concentrated. Purification by flash chromatography (5% MeOH/CH₂Cl₂) gave a foam. Trituration with 10% EtOAc/ether gave 0.145 g (25%) of product as an off-white solid, mp 189°-191° C.

¹H NMR (DMSO-d₆) d 2.55 (s, 3H), 2.82 (t, J=7.0 Hz, 2H), 3.07 (t, J=7.0 Hz, 2H), 5.20 (s, 2H), 7.31 (d, J=8.0 Hz, 1H), 7.65 (m, 5H), 8.39 (s, 1H).

Anal. calcd for $C_{22}H_{17}F_3N_8O$: C, 56.65; H, 3.67; N, 24.03 Found: C, 56.22; H, 4.11; N, 23.44.

EXAMPLE 7

2,4-Dimethyl-5,6,8-trihydro-8-[[5-[2-(1H-tetrazol-5-yl)phenyl]-2-pyridinyl]methyl]-7H-pyrido[2,3-d]pyrimidin-7-one Step 1) (6-Methylpyridin-3-yl)trifluoromethanesulfonate To a stirred, cooled (0° C.) solution of 3-hydroxy-6-methylpyridine (14.0 g, 0.128 mol) in pyridine (70 mL) was added trifluoromethanesulfonic anhydride (39.8 g, 0.141 mol) dropwise. The mixture was stirred at room temperature for 5 h. Water was added and the mixture was extracted with ether. The extracts were washed with brine, dried (MgSO₄), and concentrated to give 27.3 g (88%) of product as a brown oil.

¹H NMR (CMSO-d₆): d 2.50 (s, 3H), 7.45 (d, J=9.2 Hz, 1H), 7.90 (dd, J=9.2 Hz, 2.3 Hz, 1H), 8.60 (d, J=2.3 Hz, 1H).

Step 2) (6-Methylpyridin-3-yl)trifluoromethanesulfonate N-Oxide

To a stirred solution of (6-methylpyridin-3-yl)trifluoromethanesulfonate (27.3 g, 0.113 mol) in CH₂Cl₂ (140 mL) was added mCPBA (21.5 g, 0.124 mol) in portions. After 16 h, the precipitate was removed by filtration and the filtrate was concentrated. Purification by flash chromatography (2% MeOH/CH$_2$Cl$_2$) gave 25.0 g (86%) of product as colorless crystals, mp 47°–48° C.

$^1$H NMR (DMSO-d$_6$): d 2.36 (s, 3H), 7.56 (dd, J=8.9 Hz, 2.3 Hz, 1H), 7.69 (d, J=8.9 Hz, 1H), 8.84 (d, J=2.3 Hz, 1H).

Step 3) (6-Hydroxymethylpyridin-3-yl)trifluoromethanesulfonate

To stirred, cooled (0° C.) (6-methylpyridin-3-yl)trifluoromethanesulfonate N-oxide (25.0 g, 0.097 mol) was added trifluoroacetic anhydride (69.0 mL, 0.487 mol) dropwise. The mixture was stirred at room temperature for 30 min then heated under reflux for 1 h. The mixture was cooled to room temperature and 10% aqueous NaHCO$_3$ (400 mL) was added. The resulting mixture was extracted with CH$_2$Cl$_2$ and the extracts were washed with brine, dried (MgSO$_4$), and concentrated. Purification by flash chromatography (2% MeOH/CH$_2$Cl$_2$) gave 10.0 g (40%) of product as a colorless oil.

$^1$H NMR (DMSO-d$_6$): d 4.60 (s, 1H), 5.60 (s, 1H), 7.64 (d, J=8.8 Hz, 1H), 8.03 (dd, J=8.8 Hz, 2.8 Hz, 1H), 8.67 (d, J=2.8 Hz, 1H).

Step 4) 2-(2-tert-Butyl-1H-tetrazol-5-yl)phenyltri-n-butylstannane

To a cooled (−78° C.) solution of 1-tert-butyl-5-(2-bromophenyl)-1H-tetrazole (12.3 g, 0.043 mol), prepared as described in Step 3 of the Example 3 alternative synthesis, in THF (80 mL) was added 1.6M nBuLi in hexanes (32.7 mL, 0.052 mol). After 1 h, tri-n-butyltin chloride (17.1 g, 0.052 mol) was added and stirring was continued for 3 h at −78° C. The mixture was warmed to room temperature and stirred for 18 h. Water was added and the mixture was extracted with ether. The combined extracts were washed with water, brine, dried (MgSO$_4$), and concentrated to give a brown oil. Excess tri-n-butyltin chloride and remaining starting material were removed by distillation under high vacuum to give 9.6 g (45%) of product as a brown oil.

$^1$H NMR (DMSO-d$_6$): d 0.78 (t, J=7.3 Hz, 9H), 0.93 (t, J=8.3 Hz, 6H), 1.21 (m, 6H), 1.43 (m, 6H), 7.43 (d, J=8.9 Hz, 1H), 7.45 (d, J=8.5 Hz, 1H), 7.60 (dd, J=8.9 Hz, 2.3 Hz, 1H), 8.0 (dd, J=8.5 Hz, 2.3 Hz, 1H).

Step 5) 2-tert-Butyl-5-[2-[(2-hydroxymethyl)pyridin-5-yl]phenyl]tetrazole

A mixture of (6-hydroxymethylpyridin-3-yl)trifluoromethanesulfonate (5.0 g, 0.019 mol), 2-(2-tert-butyl-1H-tetrazol-5-yl)phenyltri-n-butylstannane (9.5 g, 0.019 mol), bis(triphenylphosphine)palladium chloride (0.70 g, 0.97 mmol), CuI (0.37 g, 1.9 mmol), and DMF (30 mL) was heated at 100° C. for 18 h. 20% Aqueous KF was added and the mixture was stirred at room temperature for 30 min. The precipitate was removed by filtration and the filtrate was extracted with ether. The extracts were washed with NH$_4$OH, saturated aqueous NH$_4$Cl, water, brine, dried (MgSO$_4$), and concentrated. Purification by flash chromatography (5% EtOAc/hexane) gave 0.5 g (8%) of product as a yellow oil.

$^1$H NMR (DMSO-d$_6$): d 1.55 (s, 9H), 4.56 (d, J=6.0 Hz, 2H), 5.40 (t, J=6.0 Hz, 1H), 7.38 (d, J=8.8 Hz, 1H), 7.60 (m, 4H), 7.90 (dd, J=8.8 Hz, 2.3 Hz, 1H), 8.20 (d, J=2.3 Hz, 1H).

Step 6) 2-tert-Butyl-5-[2-[(2-bromomethyl)pyridin-5-yl]phenyl]tetrazole

A mixture of 2-tert-butyl-5-[2-[(2-hydroxymethyl)pyridin-5-yl]phenyl]tetrazole (0.50 g, 1.62 mmol), triphenylphosphine (0.51 g, 1.94 mmol), and CBr$_4$ (0.64 g, 1.94 mmol) in THF (30 mL) was stirred at room temperature for 16 h. The mixture was concentrated and purification by flash chromatography (20% EtOAc/hexane) gave 0.40 g (66%) of product as a colorless oil.

$^1$H NMR (DMSO-d$_6$): d 1.56 (s, 9H), 4.70 (s, 2H), 7.60 (m, 5H), 7.95 (dd, J=8.8 Hz, 1.6 Hz, 1H), 8.28 (d, J=1.6 Hz, 1H).

Step 7) 2,4-Dimethyl-5,6,8-trihydro-8-[[5-[2-(1H-tetrazol-5-yl)phenyl]-2-pyridinyl]methyl]-7H-pyrido[2,3-d]pyrimidin-7-one To a stirred suspension of NaH (60% dispersion in mineral oil; 41 mg, 1.03 mmol) in DMF (1 mL) was added 2,4-dimethyl-5,6,8-trihydro-7H-pyrido[2,3-d]pyrimidin-7-one (170 mg, 0.94 mmol), prepared as described in Step 1 of Example 5. After 30 min, a solution of 2-tert-butyl-5-[2-[(2-bromomethyl)pyridin-5-yl]phenyl]tetrazole (350 mg, 0.94 mmol) in DMF (5 mL) was added and the mixture was stirred for 3 h. The mixture was concentrated, taken up in EtOAc, and washed with water. The organic phase was dried (MgSO$_4$), concentrated, and purified by flash chromatography (3% MeOH/CH$_2$Cl$_2$) to give a yellow foam. The foam was heated in 6N HCl (2 mL) for 16 h, cooled, and the pH was adjusted to 4 with 50% NaOH. The mixture was extracted with CHCl$_3$, and the combined extracts were dried (MgSO$_4$), and concentrated. Trituration with EtOH/ether gave 40 mg (10%) of product as a white solid, mp 208°–209° C.

$^1$H NMR (DMSO-d$_6$): d 2.35 (s, 3H), 2.37 (s, 3H), 2.77 (t, J=7.9 Hz, 2H), 2.90 (t, J=7.9 Hz, 2H), 5.30 (s, 2H), 7.10 (d, J=8.8 Hz, 1H), 7.36 (dd, J=8.8 Hz, 1.6 Hz, 1H), 7.60 (m, 4H), 8.23 (d, J=1.6 Hz, 1H).

IR (KBr, cm$^{-1}$): 1690.

Anal. calcd for C$_{22}$H$_{20}$N$_8$O: C, 64.07; H, 4.89; N, 27.17. Found: C, 63.87; H, 5.16; N, 27.22.

EXAMPLE 8

2,4,6-Trimethyl-5,6,8-trihydro-8-[[2'-(1H-tetrazol-5-yl)[1,1-biphenyl]-4-yl]methyl]-7H-pyrido[2,3-d]pyrimidin-7-one Step 1) 2,4-Dimethyl-5,6,8-trihydro-8-[[2'-cyano[1,1-biphenyl]-4-yl]methyl]-7H-pyrido[2,3-d]pyrimidin-7-one To a stirred suspension of NaH (60% dispersion in mineral oil; 0.115 g, 4.80 mmol) in DMF (5 mL) was added 2,4-dimethyl-5,6,8-trihydro-7H-pyrido[2,3-d]pyrimidin-7-one (0.85 g, 4.80 mmol), prepared as described in Step 1 of Example 5. After 45 min, 2-[4-(bromomethyl)phenyl]benzonitrile (1.00 g, 3.7 mmol) in DMF (4 mL) was added and the mixture was stirred at room temperature for 18 h. Water was added and the mixture was extracted with CH$_2$Cl$_2$. The extracts were concentrated and the crude product was purified by flash chromatography (2% MeOH/CH$_2$Cl$_2$). Trituration with ether gave 0.80 g (60%) of product as a yellow solid, mp 133°–137° C.

$^1$H NMR (DMSO-d$_6$): d 2.37 (s, 2H), 2.45 (s, 3H), 2.76 (t, J=7.9 Hz, 2H), 2.88 (t, J=7.9 Hz, 2H), 5.27 (s, 2H), 7.42 (d, J=8.2 Hz, 2H), 7.50 (d, J=8.2 Hz, 2H), 7.58 (m, 2H), 7.77 (m, 1H), 7.93 (d, J=7.6 Hz, 1H).

Step 2) 2,4,6-Trimethyl-5,6,8-trihydro-8-[[2'-cyano[1,1-biphenyl]-4-yl]methyl]-7H-pyrido[2,3-d]pyrimidin-7-one To a cooled (−78° C.) solution of 2,4-dimethyl-5,6,8-trihydro-8-[[2'-cyano[1,1-biphenyl]-4-yl]methyl]-7H-pyrido[2,3-d]pyrimidin-7-one (0.40 g, 1.10 mmol) in THF (2.0 mL) was added LDA (2M; 0.55 mL, 1.10 mmol). After 45 min, MeI (0.16 g, 1.15 mmol) was added and the mixture was allowed to warm to room temperature and stirred for 18 h. The mixture was concentrated and partitioned between water and CH₂Cl₂. The organic phase was dried (MgSO₄) and concentrated to give an orange oil. Purification by flash chromatography (60% EtOAc/hexane) gave 0.15 g (36%) of product as a yellow solid, mp 153°–156° C.

¹H NMR (DMSO-d₆): d 1.21 (d, J=6.3 Hz, 3H), 2.37 (s, 3H), 2.44 (s, 3H), 2.60 (m, 1H), 2.80 (m, 1H), 3.05 (dd, J=9.6, 6.0 Hz, 1H), 5.21 (d, J=15.1 Hz, 1H), 7.39 (d, J=8.3 Hz, 2H), 7.49 (d, J=8.3 Hz, 2H), 7.58 (m, 2H), 7.80 (m, 1H), 7.91 (dd, J=6.9, 0.9 Hz, 1H).

Step 3) 2,4,6-Trimethyl-5,6,8-trihydro-8-[[2'-(1H-tetrazol-5-yl)[1,1-biphenyl]-4-yl]methyl]-7H-pyrido[2,3-d]pyrimidin-7-one A mixture of 2,4,6-trimethyl-5,6,8-trihydro-8-[[2'-cyano[1,1-biphenyl]-4-yl]methyl]-7H-pyrido[2,3-d]pyrimidin-7-one (0.57 g, 1.50 mmol), NaN₃ (0.13 g, 1.90 mmol), and tri-n-butyltin chloride (0.62 g, 1.90 mmol) in xylenes (5 mL) was heated under reflux for 48 h. The mixture was cooled and 1N HCl (2 mL) was added. CHCl₃ and water were added, and the organic phase was dried (MgSO₄) and concentrated. Recrystallization from EtOAc gave 0.25 g (39%) of product as a white solid, mp 161°–163° C.

¹H NMR (DMSO-d₆): d 1.19 (d, J=6.7 Hz), 2.37 (s, 3H), 2.43 (s, 3H), 2.59 (m, 1H), 2.80 (m, 1H), 3.02 (dd, J=15.7, 7.0 Hz, 1H), 5.12 (d, J=15.0 Hz, 1H), 5.22 (d, J=15.0 Hz, 1H), 7.00 (d, J=8.0 Hz, 2H), 7.18 (d, J=8.0 Hz, 2H), 7.57 (m, 2H), 7.63 (m, 2H).

EXAMPLE 9

2,4-Dimethyl-8-[[2'-(1H-tetrazol-5-yl)[1,1-biphenyl]-4-yl]methyl]-7H-pyrido[2,3-d]pyrimidin-7-one Step 1) 2,4-Dimethyl-8-[[2'-cyano[1,1-biphenyl]-4-yl]methyl]-7H-pyrido[2,3-d]pyrimidin-7-one Using the same procedure as described in Step 1 of Example 8, to a stirred suspension of NaH (60% dispersion in mineral oil) in DMF add 2,4-dimethyl-7H-pyrido[2,3-d]pyrimidin-7-one, prepared according to T. Sakamoto, et al. *Chem. Pharm. Bull.*, 1982, 30, 2410. After 45 min, add 2-[4-(bromomethyl)phenyl]benzonitrile in DMF and stir the mixture at room temperature for 18 h. Add water and extract the mixture with CH₂Cl₂. Concentrate the extracts and purify the crude product by flash chromatography (2% MeOH/CH₂Cl₂). Trituration with ether gives the product.

Step 2) 2,4-Dimethyl-8-[[2'-(1H-tetrazol-5-yl)[1,1-biphenyl]-4-yl]methyl]-7H-pyrido[2,3-d]pyrimidin-7-one Using the same procedure as described in Step 3 of Example 8, heat a mixture of 2,4-dimethyl-8-[[2'-cyano[1,1-biphenyl]-4-yl]methyl]-7H-pyrido[2,3-d]pyrimidin-7-one, NaN₃, and tri-n-butyltin chloride in xylenes under reflux for 48 h. Cool the mixture and add 1N HCl (2 mL). Add CHCl₃ and water, and dry (MgSO₄) and concentrate the organic phase. Recrystallization from EtOAc gives the product.

We claim:

1. A compound of formula I

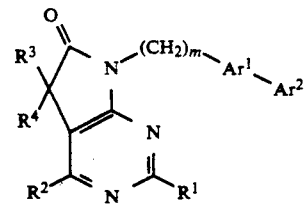

wherein R¹, R², R³, and R⁴ are independently H, lower alkyl containing 1 to 6 carbon atoms, or perfluoroalkyl containing 1 to 6 carbon atoms; m is 0 to 3; Ar¹ is

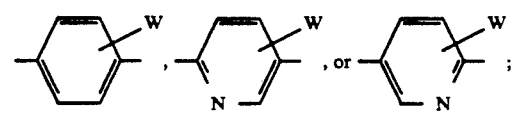

wherein W is H, lower alkyl containing 1 to 6 carbon atoms, halogen, hydroxy, or lower alkoxy containing 1 to 6 carbon atoms; Ar² is

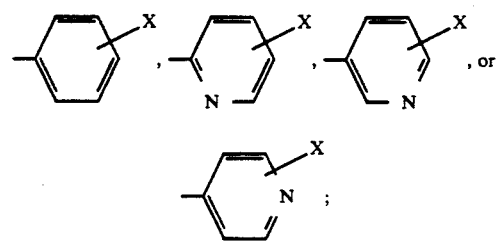

wherein X is

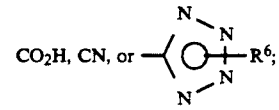

wherein R⁶ is H, tert-butyl, tri-n-butylstannyl, or triphenylmethyl; or a pharmaceutically acceptable salt thereof.

2. A compound according to claim 1 of formula II

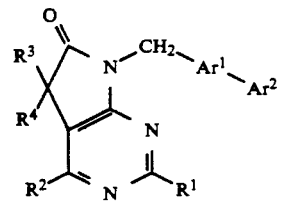

wherein R¹, R², R³, and R⁴ are independently H, lower alkyl containing 1 to 6 carbon atoms, or perfluoroalkyl containing 1 to 6 carbon atoms; Ar¹ is

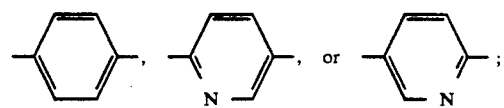

Ar² is

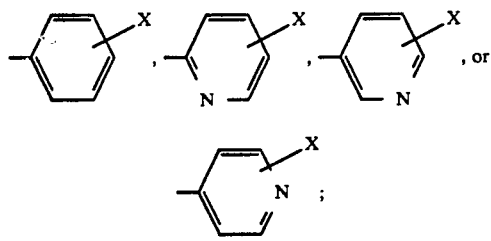

wherein X is

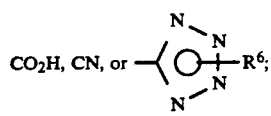

wherein R⁶ is H, tert-butyl, tri-n-butylstannyl, or triphenylmethyl; or a pharmaceutically acceptable salt thereof.

3. A compound according to claim 2 of formula III

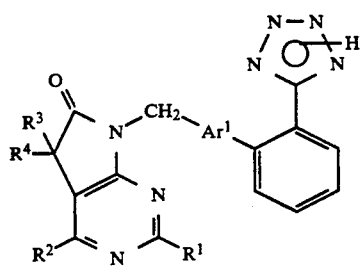

wherein $R^1$, $R^2$, $R^3$, and $R^4$ are independently H, methyl, trifluoromethyl; Ar¹ is

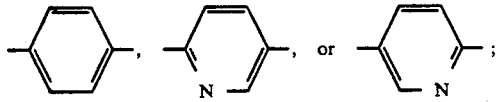

or a pharmaceutically acceptable salt thereof.

4. The compound according to claim 3 2,4-dimethyl-5,7-dihydro-7-[[2'-(1H-tetrazol-5-yl)[1,1-biphenyl]-4-yl]methyl]-6H-pyrrolo[2,3-d]pyrimidin-6-one or a pharmaceutically acceptable salt thereof.

5. The compound according to claim 3 5,7-dihydro-2-methyl-7-[[2'-(1H-tetrazol-5-yl)[1,1-biphenyl]-4-yl]methyl]-4-(trifluoromethyl)-6H-pyrrolo[2,3-d]pyrimidin-6-one or a pharmaceutically acceptable salt thereof.

6. A method of treating humans suffering from hypertension by administering an effective amount of the compound of claim 1.

7. A method of treating humans suffering from congestive heart failure by administering an effective amount of the compound of claim 1.

8. A pharmaceutical composition comprising an effective amount of a compound of formula I

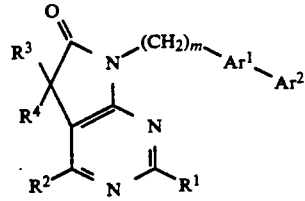

wherein $R^1$, $R^2$, $R^3$, $R^4$ are independently H, lower alkyl containing 1 to 6 carbon atoms, or perfluoroalkyl containing 1 to 6 carbon atoms; m is 0 to 3; Ar¹ is

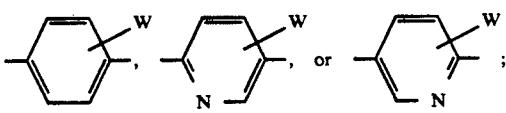

wherein W is H, lower alkyl containing 1 to 6 carbon atoms, halogen, hydroxy, or lower alkoxy containing 1 to 6 carbon atoms; Ar² is

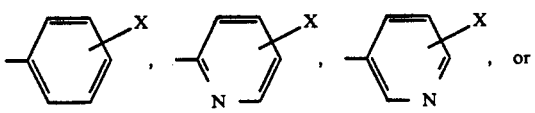

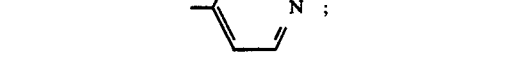

wherein X is

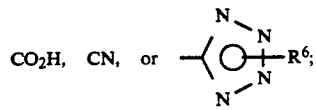

wherein R⁶ is H, tert-butyl, tri-n-butylstannyl, or triphenylmethyl; or a pharmaceutically acceptable carrier.

* * * * *